United States Patent [19]

Calanni

[11] 4,387,713
[45] Jun. 14, 1983

[54] DISPOSABLE DISCHARGE COLLECTOR FOR A DRAINABLE STOMA POUCH WITH WIPER

[76] Inventor: John R. Calanni, 413 S. Diamond St., Ravenna, Ohio 44266

[21] Appl. No.: 284,409

[22] Filed: Jul. 17, 1981

[51] Int. Cl.³ .............................................. A61F 5/44
[52] U.S. Cl. .................................... 604/333; 128/760; 604/336; 604/335; 604/339
[58] Field of Search ............... 128/760, 765, 766, 767, 128/283, 272, 272.1, 272.3, 275, DIG. 24, DIG. 28; 150/2.7, 3; 141/10, 114, 313–317; 222/95, 103; 604/277, 327, 332, 334, 335, 350, 323, 355

[56] References Cited

U.S. PATENT DOCUMENTS

| | | | |
|---|---|---|---|
| 708,549 | 9/1902 | Heiliger | 150/2.7 |
| 3,089,493 | 5/1963 | Galindo | 128/283 |
| 3,312,221 | 4/1967 | Overment | 128/275 |
| 3,802,418 | 4/1974 | Clayton | 128/283 |
| 3,825,005 | 7/1974 | Fonton | 128/283 |
| 3,841,332 | 10/1974 | Treacle | 150/2.7 |

Primary Examiner—Richard J. Apley
Assistant Examiner—J. L. Kruter
Attorney, Agent, or Firm—Hamilton, Renner & Kenner

[57] ABSTRACT

A disposable discharge collector (10) for a stoma pouch (23) having a drain opening (32) therein includes a bag body (11) having flexible walls (14,15) and an opening (16) therein suitable to receive the drain opening (32) of the stoma pouch (23), a locking mechanism (12) adjacent the opening (16) for providing a liquid-tight closure of the bag body (11), and a wiper mechanism (13) in fixed, proximate spatial relation beneath the locking mechanism (12) and interior to bag body (11) for manually forcing substantially all discharge (24) in the stoma pouch (23) into bag body (11) without spillage, permitting the sanitary disposal of discharge (24).

10 Claims, 4 Drawing Figures

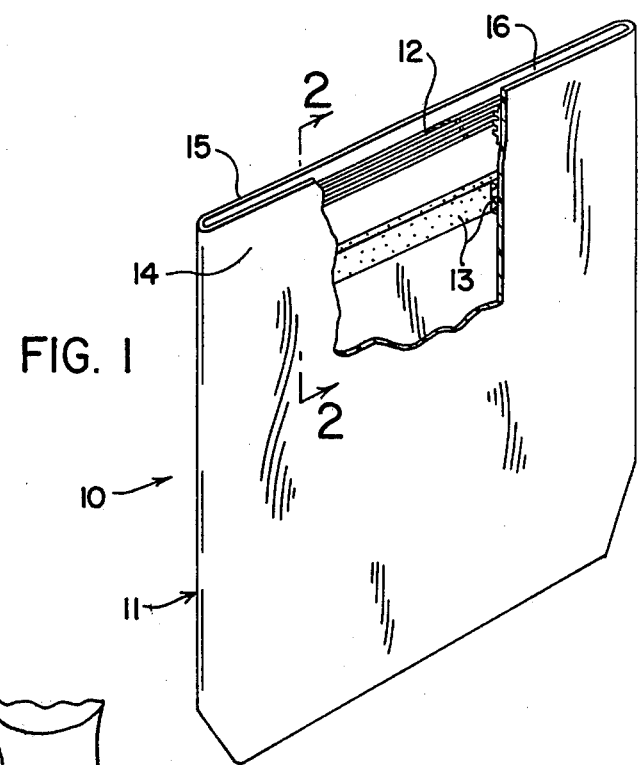
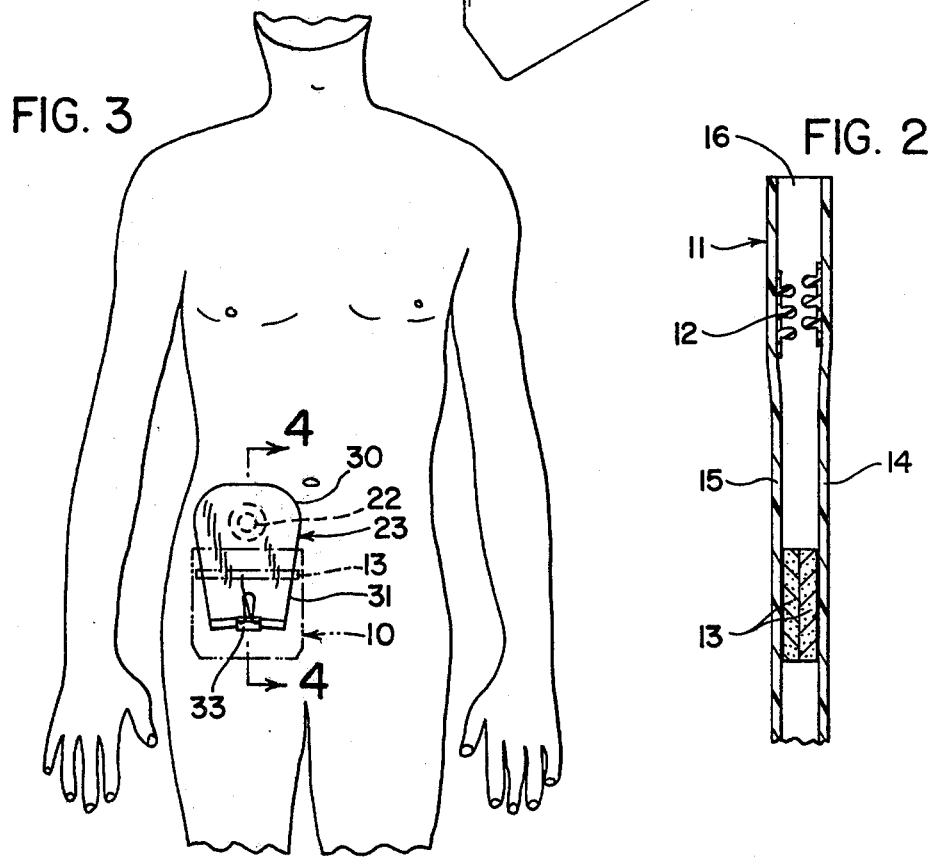

DISPOSABLE DISCHARGE COLLECTOR FOR A DRAINABLE STOMA POUCH WITH WIPER

TECHNICAL FIELD

The present invention relates generally to appliances for use by persons having had surgical modifications to their digestive tracts. More particularly, the present invention relates to pouches that receive intestinal effluent via a surgically provided, bud-like opening in the abdomen known as a stoma. More specifically, the present invention pertains to devices for collecting the digestive tract discharge in drainable stoma pouches.

BACKGROUND ART

Many persons for an array of medical reasons not relevant herein require that their digestive tracts at some point be surgically terminated through the abdominal wall, rather than through the rectum and anus. Called an ileostomy when the last section of the small intestine known as the ileum is opened and brought to the abdominal surface, and called a colostomy when it is the colon that is opened and brought to the abdominal surface, these surgical procedures result in a bud-like opening in the abdomen known as a stoma through which evacuation of all remaining digestive products thereafter occur.

Inasmuch as the stoma contains no sphincter muscle to permit excretion control of the remaining digestive products, it is necessary to provide some appliance unobtrusively under the wearer's clothing, commonly referred to as a stoma pouch, to collect and contain the effluent. When the stoma pouch is filled to its maximum capacity it must be replaced, using appropriate methods to insure that the skin surrounding the stoma be kept meticulously clean to avoid irritation and infection. Unfortunately, quite often the stoma pouch fills to its capacity when it is inconvenient or impossible for the wearer to replace the same, especially while maintaining any semblance of sanitation. Accordingly, stoma pouches have been designed with recloseable, tapered openings for draining the contents thereof. Amazingly, however, to my knowledge the only device heretofore used to collect and dispose of the discharge in the stoma pouch has been the ordinary paper cup.

The utilization of a disposable cup to collect and dispose of discharge in the stoma pouch presents numerous inconveniences, difficulties and sanitary hazards. For example, it is at least inconvenient and discomforting to have to use one's bare hand to force discharge through the stoma pouch drain and into the cup. Depending upon the configurations involved, it is often difficult to fit the stoma pouch tapered drain into the cup and maintain it therein during drainage of the stoma pouch. Indeed, if miraculously spillage does not occur during this drainage process, discharge almost certainly will be deposited on the outside of the stoma pouch and/or on the wearer's hand, both unpleasant and sanitarily deleterious, and requiring further laborious and possibly embarrassing clean-up measures. Additionally, the indiscriminate disposal of the discharge-filled cup is exceedingly troublesome as there is no effective mechanism for providing a liquid-tight closure of the cup and because the discharge remains in plain view, discomforting to some stoma pouch wearers and most other persons.

DISCLOSURE OF THE INVENTION

It is, therefore, an object of the invention to provide a disposable discharge collector for a drainable stoma pouch into which may be emptied without spillage all the discharge from the stoma pouch while maintaining completely sanitary conditions.

It is another object of the invention to provide a disposable discharge collector for a drainable stoma pouch, as set forth above, which includes a liquid-tight locking mechanism integral therewith to permit the convenient disposal of the discharge collector without spillage.

It is still another object of the invention to provide a disposable discharge collector for a drainable stoma pouch, as set forth above, which includes a wiper mechanism to facilitate emptying of discharge from the stoma pouch into the collector while maintaining completely sanitary conditions.

It is yet another object of the invention to provide a disposable discharge collector for a drainable stoma pouch, as set forth above, in which the wiper mechanism precludes spillage of discharge on the locking mechanism, which spillage could prevent the proper functioning of the locking mechanism.

It is a further object of the invention to provide a disposable discharge collector for a drainable stoma pouch, as set forth above, that is usable with substantially all known configurations of drainable stoma pouches.

It is still a further object of the invention to provide a disposable discharge collector for a drainable stoma pouch, as set forth above, which is opaque so as to preclude unwanted viewing of the discharge.

These and other objects and advantages of the present invention over existing prior art forms will become more apparent and fully understood from the following description in conjunction with the accompanying drawings.

In general, a disposable discharge collector for a stoma pouch having a drain opening therein includes a bag body for receiving the discharge from the stoma pouch and permitting the sanitary disposal thereof, the bag body having flexible walls and an opening therein suitable to receive the opening end of the stoma pouch, a locking mechanism adjacent the bag body opening for providing a liquid-tight closure of the bag body, and a wiper mechanism in fixed, proximate spatial relation to the locking mechanism for manually forcing substantially all discharge in the stoma pouch into the discharge collector without spillage.

BRIEF DESCRIPTION OF THE DRAWINGS

FIG. 1 is a perspective view of a disposable discharge collector for a drainable stoma pouch in accordance with the concept of the present invention, depicting through a cut-away section therein exemplary locking and wiper mechanisms in fixed, proximate spatial relation.

FIG. 2 is a section taken substantially along the line 2—2 of FIG. 1 illustrating a portion of the disposable discharge collector for a stoma pouch and exemplary locking and wiper mechanisms affixed thereto.

FIG. 3 is an elevational view of a person having a stoma and showing a conventional drainable stoma pouch attached thereto, the positioning of the disposable discharge collector during initial drainage of the stoma pouch also being shown therein in phantom.

PREFERRED EMBODIMENT FOR CARRYING OUT THE INVENTION

Figure 4:
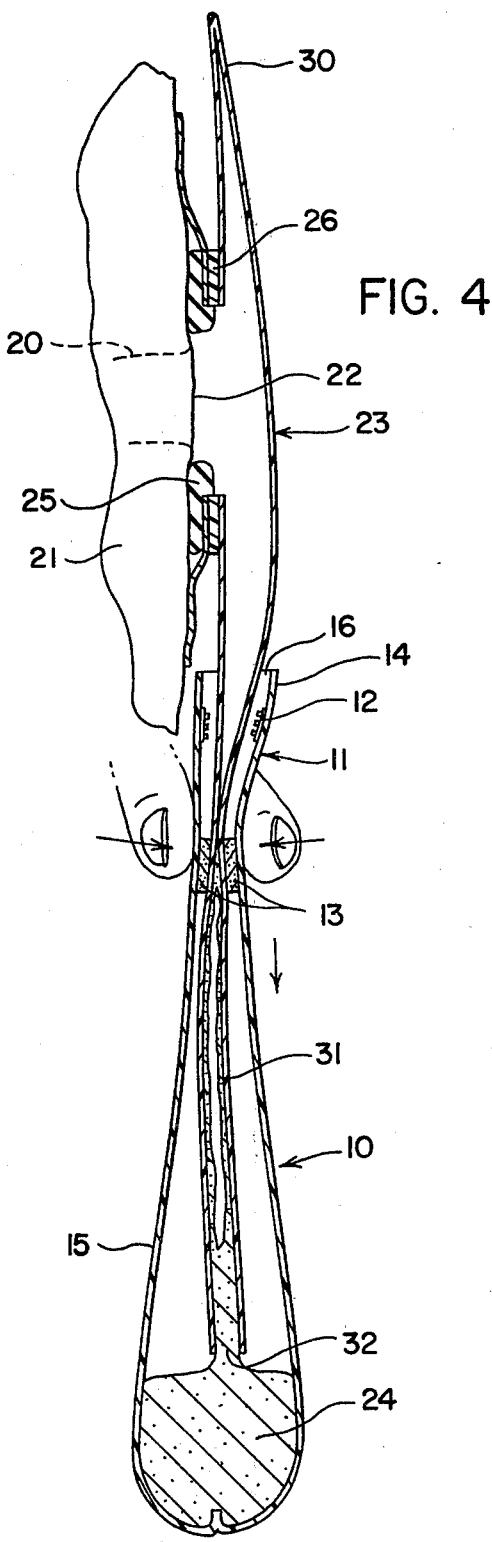
FIG. 4 is a section taken substantially along the line 4—4 of FIG. 3 illustrating the process of draining discharge from the stoma pouch by use of the exemplary disposable discharge collector of FIG. 1.

FIG. 1 depicts in perspective a disposable discharge collector, generally indicated by the numeral 10, for a drainable stoma pouch. Referring to both FIGS. 1 and 2, discharge collector 10 may be seen to include bag body 11, locking mechanism 12 and wiper mechanism 13.

Bag body 11 may be similar to a conventional food storage bag having a flexible, plastic film first wall 14 and a like second wall 15 opposite thereto integrally joined at one, say lower, edge by any suitable means not relevant herein, and having an opening 16 at the opposite, say upper, end. Bag body 11 should preferably be of opaque material to preclude any inadvertent viewing of any discharge therein, and most desirably has a sufficiently wide opening 16 to permit insertion of any tapered stoma pouch drain to a point in the stoma pouch immediately below the point of its connection to the stoma, as further delineated hereinafter.

Any known locking mechanism that provides liquid-tight closure of the bag body 11 is suitable for use within discharge collector 10. The releasably interlocking rib and groove element design of U.S. Pat. No. Re. 28,969 has been found particularly acceptable for use in the present environment, although non-integrally formed, one-time closure mechanisms are also permissible for inclusion with discharge collector 10. Locking mechanism 12 is to be positioned adjacent opening 16 and preferably but not necessarily interior to walls 14, 15 of bag body 11. In the depicted embodiment where bag body 11 is substantially rectangular and opening 16 extends linearly the length of one side, locking mechanism 12 should be optimum performance also extend linearly parallel to opening 16.

Wiper mechanism 13 may be made of any material and be of any profile as would occur to the ordinarily skilled artisan in effectuating the forced removal of all discharge in the stoma pouch by the gentle pinching of the upper ends thereof as described in detail hereinafter. A pliant material as felt formed in a bar of rectangular profile has been successfully utilized in discharge collector 10 as wiper mechanism 13. For reasons which will become apparent hereinafter, wiper mechanism 13 is either by suitable means as adhesion affixed to or manufactured integrally with the interior of walls 14, 15 in fixed, proximate spatial relation with locking mechanism 12. In the present instance, adhesion of the felt bar parallel with and spaced approximately one inch below locking mechanism 12 yields successful results in operation.

Where desired, ample quantities of a suitable deodorant may be placed within bag body 11 to mask any unpleasant odors emanating from the discharge taken from the stoma pouch.

The operation of discharge collector 10 may be best understood by reference to FIGS. 3 and 4 wherein an elevational view and a select corresponding sectional view is shown of a person having had a surgical procedure whereby some portion of the digestive tract 20 is brought to the abdominal surface 21 at stoma 22. A conventional drainable stoma pouch 23 for collection of discharge 24 is affixed to stoma 22 by means of an annular, karaya gum gasket 25 having flange ring 26 for interference coupling to the gasket 25 body. Stoma pouch 23 includes a somewhat semicircular upper portion 30 and a tapered lower portion 31 truncated in an opening 32 through which discharge 24 may pass. The lower portion 31 of stoma pouch 23 is rolled up and secured by any suitable means as spring clip 33 during all times other than when stoma pouch 23 is being emptied, thereby completely sealing stoma pouch 23 for collection and containment of discharge 24.

As discharge 24 is emitted from the digestive tract through stoma 22 into stoma pouch 23, gravity will force its collection in tapered lower portion 31. When tapered lower portion 31 is filled with discharge 24 to a level slightly beneath gasket 25, the wearer removes spring clip 33 and slips tapered lower portion 31 through opening 16 of the discharge collector 10 and down into the interior thereof until wiper mechanism 13 is just above the highest level of discharge 24. Grasping discharge collector 10 at opposite sides of the bag body 11 with the thumb and index finger of each hand aligned with the upper side of wiper mechanism 13, the wearer simply applies moderate downwardly directed compressive force upon wiper mechanism 13, pinching the same at its upper side and forcing it into an inverted, slightly V-shaped wedge which drives downwardly substantially all discharge 24 residing in tapered lower portion 31. As discharge 24 is driven forward, tapered lower portion 31 unfolds and all discharge 24 forced into discharge collector 10 beneath the wiper mechanism 13. Once wiper mechanism 13 is forced past opening 32, locking mechanism 12 may be operated to seal discharge collector 10 and discharge collector 10 safely discarded. Tapered lower portion 31 is refolded and spring clip 33 reapplied to reclose stoma pouch 23.

It should now be evident that as the wearer contacts only the outside of discharge collector 10 above wiper mechanism 13, the wearer remains completely clean and spillage is entirely eliminated. Moreover, since locking mechanism 12 is in spatial relation above wiper mechanism 13, virtually no discharge 24 can escape to interfere with the operation of the locking mechanism 12. Beyond this, since tapered lower portion 31 is progressively withdrawn from the interior of bag body 11 as the latter fills with discharge 24, the exterior of stoma pouch 23 remains completely dry and sanitary, a virtually impossible task using the prior art device.

It now should be understandable that so long as the frictional force of wiper mechanism 13 would not become too great when in use, wiper mechanism 13 may be made of any material and in any desired profile, by way of example only, as triangular instead of rectangular.

Inasmuch as the present invention is subject to many variations, modifications and changes in detail, a number of which have been expressly stated herein, it is intended that all matter described throughout this entire specification or shown in the accompanying drawings be interpreted as illustrative and not in a limiting sense. It should thus be evident that a device constructed according to the concept of the present invention, and reasonably equivalent thereto, will accomplish the objects of the present invention and otherwise substantially improve the art of collecting the disposing of the discharge in a drainable stoma pouch.

I claim:

1. A disposable discharge collector for a stoma pouch having a drain opening therein, comprising:

bag body means for receiving the discharge from the stoma pouch and permitting the sanitary disposal thereof, said bag body means having flexible walls and an opening therein suitable to receive the drain opening end of the stoma pouch, locking means adjacent said bag body opening for providing a liquid-tight closure of said bag body, and wiper means in fixed, proximate spatial relation to said locking means for forcing with a continuous manual stroke over the stoma pouch substantially all discharge in the stoma pouch into the discharge collector without spillage.

2. A disposable discharge collector, as set forth in claim 1, wherein the stoma pouch has a tapered drainage cone and said opening in said bag body means is configured to permit the insertion of said tapered drainage cone into the interior of said bag body means past said locking means whereby said wiper means precludes spillage of the discharge upon said locking means.

3. A disposable discharge collector, as set forth in claim 2, wherein said wiper means is affixed to the interior of said flexible walls.

4. A disposable discharge collector, as set forth in claim 2, wherein said wiper means is integrally part of said flexible walls on facing inner surfaces thereof.

5. A disposable discharge collector, as set forth in claims 3 or 4, wherein said bag body means is opaque.

6. A disposable discharge collector, as set forth in claim 5, wherein said opening of said bag body means is linear, said locking means extending substantially the entire length of said opening in said bag body means and having a longitudinal axis parallel with said opening in said bag body means and adjacent thereto, said wiper means having a longitudinal axis parallel with and beneath said locking means.

7. A disposable discharge collector, as set forth in claim 6, wherein said wiper means is substantially rectangular in cross-section and is formed of a compressible material.

8. A disposable discharge collector, as set forth in claim 6, wherein said bag body means includes deodorant means in the interior thereof for masking any odor of the discharge.

9. A disposable discharge collector, as set forth in claim 6, wherein said bag body means is substantially rectangular and said opening in said bag body means extends the length of one side thereof.

10. A disposable discharge collector, as set forth in claim 9, wherein said locking means is integrally formed with said flexible walls on facing inner surfaces thereof.

* * * * *

UNITED STATES PATENT AND TRADEMARK OFFICE
CERTIFICATE OF CORRECTION

PATENT NO. : 4,387,713
DATED : June 14, 1983
INVENTOR(S) : John R. Calanni

It is certified that error appears in the above-identified patent and that said Letters Patent are hereby corrected as shown below:

Cover page, in the title, delete the words "WITH WIPER"

Column 1, line 2, delete the words "WITH WIPER"

Column 3, line 39, "be" should read --for--

Column 4, line 28, "forward" should read --downward--; line 64, "the" (second occurrence) should read --and--

Signed and Sealed this

Twenty-ninth Day of January 1985

[SEAL]

Attest:

DONALD J. QUIGG

Attesting Officer       Acting Commissioner of Patents and Trademarks